(12) United States Patent
Harris et al.

(10) Patent No.: US 6,664,331 B2
(45) Date of Patent: Dec. 16, 2003

(54) POLY(ETHYLENE GLYCOL) DERIVATIVES WITH PROXIMAL REACTIVE GROUPS

(75) Inventors: J. Milton Harris, Huntsville, AL (US); Antoni Kozlowski, Huntsville, AL (US)

(73) Assignee: Nektar Therapeutics AL, Corporation, Huntsville, AL (US)

(*) Notice: Subject to any disclaimer, the term of this patent is extended or adjusted under 35 U.S.C. 154(b) by 0 days.

(21) Appl. No.: 09/992,102

(22) Filed: Nov. 5, 2001

(65) Prior Publication Data
US 2002/0040076 A1 Apr. 4, 2002

Related U.S. Application Data

(62) Division of application No. 09/265,989, filed on Mar. 11, 1999, now Pat. No. 6,362,254.
(60) Provisional application No. 60/077,700, filed on Mar. 12, 1998.

(51) Int. Cl.⁷ .................. A61K 31/77; C08G 65/48; C08G 81/00
(52) U.S. Cl. .................. 525/54.1; 525/403; 530/816; 424/422; 424/426
(58) Field of Search ............... 525/54.1, 403; 530/816; 424/422, 426

(56) References Cited

U.S. PATENT DOCUMENTS

| 4,179,337 A | 12/1979 | Davis et al. |
| 5,162,430 A | 11/1992 | Rhee et al. |
| 5,283,339 A | 2/1994 | Arnold et al. |
| 5,739,208 A | 4/1998 | Harris |
| 6,153,655 A | 11/2000 | Martinez et al. |
| 6,258,351 B1 * | 7/2001 | Harris .................. 424/78.3 |

FOREIGN PATENT DOCUMENTS

| EP | 0 605 963 | 7/1994 |
| EP | 0 839 849 | 5/1998 |
| WO | WO 96/21469 | 7/1996 |
| WO | WO 97/03106 | 1/1997 |

OTHER PUBLICATIONS

J.M. Harris, "Laboratory Synthesis of Polyethylene Glycol Derivatives," *Journal of Macromolecular Science–Reviews in Macromolecular Chemistry*, vol. C–25, No. 3, pp. 325–373, Jan. 1, 1985.

J.M. Harris, Ed., "Biomedical and Biotechnical Applications of Poly(Ethylene Glycol) Chemistry", Plenum, New York, pp. 1–14, 1992.

Greenwald et al., Highly Water Soluble Taxol Derivatives: 7–Polyethylene Glycol Carbamates and Carbonates:, *J.Org.Chem.*, vol. 60, No. 2, pp. 331–336, 1995.

Matsushima et al., "Modification of E. Coli Asparaginase with 2,4–Bis(O–Methoxypolyethylene Glycol)–6–Chloro–S–Triazine (Activated $PEG_2$); Disapperance of Binding Ability Towards Anti–Serum and Retention of Enzymic Activity," *Chemistry Letters*, pp. 773–776, 1980.

Nathan et al., "Copolymers of Lysine and Polyethylene Glycol: A New Family of Functionalized Drug Carriers," *Bioconjugate Chem.* 4, 54–62 (1993).

* cited by examiner

Primary Examiner—Nathan M. Nutter
(74) Attorney, Agent, or Firm—Alston & Bird LLP

(57) ABSTRACT

An activated, substantially water soluble poly(ethylene glycol) is provided having of a linear or branched poly(ethylene glycol) backbone and at least one terminus linked to the backbone through a hydrolytically stable linkage, wherein the terminus is branched and has proximal reactive groups. The free reactive groups are capable of reacting with active moieties in a biologically active agent such as a protein or peptide thus forming conjugates between the activated poly(ethylene glycol) and the biologically active agent.

53 Claims, No Drawings

POLY(ETHYLENE GLYCOL) DERIVATIVES WITH PROXIMAL REACTIVE GROUPS

CROSS-REFERENCE TO RELATED APPLICATIONS

This application is a divisional of U.S. application Ser. No. 09/265,989, now U.S. Pat. No. 6,362,254 B2, filed on Mar. 11, 1999, which is related to Provisional Application Serial No. 60/077,700, filed Mar. 12, 1998, and claims the benefit of its filing date under 35 U.S.C. §119(e). Both applications are incorporated by reference herein in their entirety.

FIELD OF THE INVENTION

This invention relates to derivatives of polyethylene glycol and related hydrophilic polymers suitable for chemical coupling to another molecule, including, for example, proteins, enzymes, small drugs, and the like.

BACKGROUND OF THE INVENTION

Chemical attachment of the hydrophilic polymer poly(ethylene glycol) ("PEG") to molecules and surfaces is of great utility in biotechnology. In its most common form PEG is a linear polymer terminated at each end with hydroxyl groups:

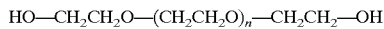

This polymer can be represented in brief form as HO—PEG—OH where it is understood that the —PEG— symbol represents the following structural unit:

In typical form n ranges from about 10 to about 2000.

PEG is commonly used as methoxy PEG-OH, or mPEG in brief, in which one terminus is the relatively inert methoxy group, while the other terminus is a hydroxyl group that is subject to ready chemical modification.

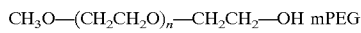

PEG is also commonly used in branched forms that can be prepared by addition of ethylene oxide to various polyols, such as glycerol, pentaerythritol and sorbitol. For example, the four-arm, branched PEG prepared from pentaerythritol is shown below:

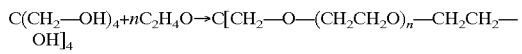

The branched PEGs can be represented in general form as $R(—PEG—OH)_n$ in which R represents the central "core" molecule, such as glycerol or pentaerythritol, and n represents the number of arms.

Branched PEGs can also be prepared in which two PEG "arms" are attached to a central linking moiety having a single functional group capable of joining to other molecules; e.g., Matsushima et al., (Chem. Lett., 773, 1980) have coupled two PEGs to a central cyanuric chloride moiety.

PEG is a well known polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, it has been shown that the water-insoluble drug paclitaxel, when coupled to PEG, becomes water-soluble. Greenwald, et al., *J. Org. Chem.*, 60:331–336 (1995).

In related work, U.S. Pat. No. 4,179,337 to Davis et al. discloses that proteins coupled to PEG have enhanced blood circulation lifetime because of reduced rate of kidney clearance and reduced immunogenicity. These and other applications are also described in *Biomedical and Biotechnical Applications of Polyethylene Glycol Chemistry*, J. M. Harris, Ed., Plenum, N.Y. (1992), and Poly(ethylene glycol) *Chemistry and Biological Applications*, J. M. Harris and S. Zalipsky, Eds., ACS, Washington D.C. (1997).

To couple PEG to a molecule such as a protein, it is often necessary to "activate" the PEG to prepare a derivative of the PEG having a functional group at the terminus. The functional group can react with certain moieties on the protein such as an amino group, thus forming a PEG-protein conjugate. Many activated derivatives of PEG have been described. An example of such an activated derivative is the succinimidyl succinate "active ester":

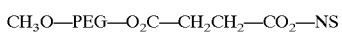

where NS=

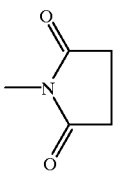

Hereinafter, the succinimidyl active ester moiety will be represented as —$CO_2$—NS in chemical drawings.

The succinimidyl active ester is a useful compound because it reacts rapidly with amino groups on proteins and other molecules to form an amide linkage (—CO—NH—). For example, U.S. Pat. No. 4,179,337 to Davis et al. describes coupling of this derivative to proteins (represented as PRO—$NH_2$):

Bifunctional PEGs with active groups at both ends of the linear polymer chain are also useful compounds when formation of a crosslinked insoluble network is desired. Many such bifunctional PEGs are known in the art. For example, U.S. Pat. No. 5,162,430 to Rhee, et al. discloses using such bifunctional PEGs to crosslink collagen.

Reactive PEGs have also been synthesized in which several active functional groups are placed along the backbone of the polymer. For example, lysine-PEG conjugates have been prepared in the art in which a number of activated groups are placed along the backbone of the polymer. Zalipsky et al. *Bioconjugate Chemistry*, 4:54–62 (1993).

U.S. Pat. No. 5,283,339 to Arnold et al. discloses PEG compounds capable of chelating metals. The PEG compounds have a terminal metal chelating group which has two free carboxylic acid or amino groups, typically linked to a nitrogen atom. The PEG compounds are used to extract and precipitate proteins from solutions with the carboxylic acid or amino groups together with the nitrogen atom capable of forming ionic complexes with metal ions. However, the metal chelating groups disclosed in the patent generally are not useful in covalently coupling the PEG compounds to proteins, peptides, or small drugs bearing functional groups such as amines. The patent does not teach forming an activated PEG derivative for covalently coupling to another molecule to form a conjugate.

SUMMARY OF THE INVENTION

The invention described herein provides a water soluble polymer such as poly(ethylene glycol) or related polymers that have a branched moiety at one end of the polymer chain and two free reactive groups linked to the branched moiety for covalent attachment to another molecule. Each reactive moiety can have a tethering group, such as an alkyl chain, linking a reactive group to the branched moiety. Thus, the branched terminus allows the activated water soluble polymer of this invention to react with two molecules to form conjugates.

Because a tethering group having a desirable length can be selected in preparing an activated polymer, the two reactive groups can be held at a predetermined distance apart from each other. The two molecules conjugated to the activated polymer through the two reactive groups can also be held at a predetermined distance apart. Accordingly, an activated PEG is provided in accordance with the invention having two free reactive moieties branching out from one PEG chain at a branched moiety. The two free reactive moieties are capable of reacting with biologically active agents such as proteins, thereby linking the activated polymer to the biologically active agents.

In accordance with one embodiment of this invention, an activated water soluble polymer is provided having the formula:

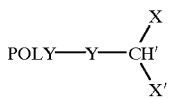

wherein POLY is a water soluble, substantially non-immunogenic polymer backbone, Y is a hydrolytically stable linkage, X and X' are reactive groups capable of reacting with a moiety in another molecule such as a protein. Typically, the polymer backbone is selected from the group consisting of linear and branched poly(ethylene glycol), linear and branched poly(alkylene oxide), linear and branched poly(vinyl pyrrolidone), linear and branched poly (vinyl alcohol), linear and branched polyoxazoline, linear and branched poly(acryloylmorpholine), and derivatives thereof. Preferably, the polymer backbone is poly(ethylene glycol) or a derivative thereof. The polymer backbone POLY can have a capping group selected from the group consisting of —OH, alkyls, and —Y—CHXX' wherein Y, X and X' are as described above and can be the same or different on each terminus of the PEG.

In a preferred embodiment, X and X' are represented by —W—Z and —W'—Z' respectively, in which Z and Z' represent reactive moieties for conjugating the polymer to another molecule. W and W' represent tethering groups comprising a substantially linear chain of atoms, e.g., alkyl chains, ether chains, ester chains, amide chains, and combinations thereof. Examples of the reactive moieties include, but are not limited to, active esters, active carbonates, aldehydes, isocyanates, isothiocyanates, epoxides, alcohols, maleimides, vinylsulfones, hydrazides, dithiopyridines, and iodoacetamides.

In another embodiment of the activated polymer of this invention, the activated water soluble polymer has the formula:

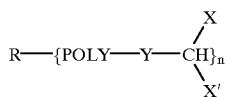

wherein
 R is a central branch core;
 POLY is a water soluble substantially non-immunogenic polymer;
 Y is a hydrolytically stable linkage;
 n is from 2 to 200;
 X and X' are reactive groups capable of reacting with a moiety in another molecule such as a protein.

Many central branch core molecules for preparing branched or dendritic PEGs are known and can all be used for R. Typically, R can be a moiety derived from lysine, glycerol, pentaerythritol, or sorbitol. Suitable polymer backbones include, but are not limited to, linear and branched poly(ethylene glycol), linear and branched poly(alkylene oxide), linear and branched poly(vinyl pyrrolidone), linear and branched poly(vinyl alcohol), linear and branched polyoxazoline, linear and branched poly (acryloylmorpholine), and derivatives thereof. Preferably, poly(ethylene glycol) or a derivative thereof is used as the polymer backbone.

The reactive groups X and X' can be reactive moieties directly linked to the branching moiety —CH. Preferably, X and X' have a tethering group and are represented by —W—Z and —W'—Z' respectively, in which Z and Z' represent reactive groups for conjugating the polymer to another molecule. W and W' represent tethering groups comprising a substantially linear chain of atoms, e.g., alkyl chains, ether chains, ester chains, amide chains, and combination thereof. Examples of the reactive groups include, but are not limited to, active esters, active carbonates, aldehydes, isocyanates, isothiocyanates, epoxides, alcohols, maleimides, vinylsulfones, hydrazides, dithiopyridines, and iodoacetamides.

The activated water soluble polymer can be covalently linked to a biologically active agent to form a conjugate. A suitable biologically active agent can be any of those having a moiety capable of reacting with at least one of the two reactive groups in the terminus of the activated polymer. The biologically active agent can have two such moieties and each of them can be linked to one of the two reactive groups. Alternatively, the conjugate can have two biologically active agents each being linked to one of the two reactive moieties of the activated polymer. Because activated polymers having different tethering groups can be prepared in accordance with this invention, an activated polymer can be provided in which the two reactive groups in a terminus of the activated polymer are a desirable distance from each other. When such an activated polymer is conjugated to two biologically active agent molecules, the two molecules can be held at a desired distance apart.

Accordingly, the activated PEG can be used with greater versatility as compared to other PEG derivatives heretofore known in the art to form various conjugates with molecules such as proteins or peptides. Since PEG molecules conjugated to another molecule can impart water solubility and reduced immunogenicity to the other molecule, the activated PEG derivatives of this invention allows greater control and precision in modifying such characteristics in a conjugate.

Thus, an activated water soluble polymer having proximal reactive groups is provided. The polymer backbone has at least one terminus having two reactive groups. The terminus has a branching moiety and two free reactive moieties linked to the branching moiety. The branching moiety is in turn linked to the polymer backbone through a stable linkage.

DETAILED DESCRIPTION OF THE INVENTION

The terms "group," "functional group," "moiety," "active moiety," "reactive site," reactive group" and "reactive moiety" are used in the art and herein to refer to distinct, definable portions or units of a molecule. The terms are somewhat synonymous in the chemical arts and are used herein to indicate that the portions of molecules that perform some function or activity and are reactive with other portions of molecules.

The term "linkage" is used herein to refer to groups or bonds that normally are formed as the result of a chemical reaction and typically are covalent linkages. Hydrolytically stable linkages means that the linkages are substantially stable in water and do not react with water at useful pHs, e.g., under physiological conditions for an extended period of time, preferably indefinitely.

The term "biologically active agent" when used herein means any substance which can affect any physical or biochemical properties of a biological organism, including but not limited to viruses, bacteria, fungi, plants, animals, and humans. In particular, as used herein, biologically active agent includes any substance intended for the diagnosis, cure, mitigation, treatment, or prevention of disease in humans or other animals, or to otherwise enhance physical or mental well being of humans or animals. Examples of biologically active agents include, but are not limited to, organic and inorganic compounds, proteins, peptides, lipids, polysaccharides, nucleotides, DNAs, RNAs, other polymers, and derivatives thereof. Examples of biologically active agents include antibiotics, fungicides, anti-viral agents, anti-inflammatory agents, anti-tumor agents, cardiovascular agents, anti-anxiety agents, hormones, growth factors, steroidal agents, and the like. Other examples include, microorganisms such as bacteria and yeast cells, viral particles, plant or animal or human cells, and the like.

The polymer backbone is a water soluble substantially non-immunogenic polymer, and is preferably poly(ethylene glycol) (PEG). However, it should be understood that other related polymers are also suitable for use in the practice of this invention and that the use of the term PEG or poly (ethylene glycol) is intended to be inclusive and not exclusive in this respect.

Poly(ethylene glycol) or PEG is useful in biological applications because it has properties that are highly desirable and is generally approved for biological or biotechnical applications. PEG typically is clear, colorless, odorless, soluble in water, stable to heat, inert to many chemical agents, does not hydrolyze or deteriorate, and is generally nontoxic. Poly(ethylene glycol) is considered to be biocompatible, which is to say that PEG is capable of coexistence with living tissues or organisms without causing harm. More specifically, PEG is non-immunogenic, which is to say that PEG does not tend to produce an immune response in the body. When attached to a molecule having some desirable function in the body, such as a biologically active agent, to form a conjugate, the PEG tends to mask the agent and can reduce or eliminate any immune response so that an organism can tolerate the presence of the agent. Accordingly, the conjugate is substantially non-toxic. PEG conjugates tend not to produce a substantial immune response or cause clotting or other undesirable effects. PEG having the formula —CH$_2$CH$_2$O—(CH$_2$CH$_2$O)$_n$—CH$_2$CH$_2$—, where n is from about 8 to about 4000, is one useful polymer in the practice of the invention. Preferably PEG having a molecular weight of from about 200 to about 100,000 Da is used as a polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. For example, the four-arm, branched PEG prepared from pentaerythritol is shown below:

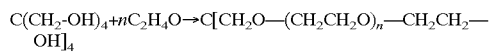

$$C(CH_2\text{-}OH)_4 + nC_2H_4O \rightarrow C[CH_2O\text{—}(CH_2CH_2O)_n\text{—}CH_2CH_2\text{—}OH]_4$$

The central branch moiety can also be derived from several amino acids, e.g., lysine.

The branched polyethylene glycols can be represented in general form as R(—PEG—OH)$_n$ in which R represents the core moiety, such as glycerol or pentaerythritol, and n represents the number of arms. Suitable branched PEGs can be prepared in accordance with International Publication No. WO 96/21469, entitled Multi-Armed, Monofunctional, and Hydrolytically Stable Derivatives of Poly(Ethylene Glycol) and Related Polymers For Modification ofsurfaces and Molecules, which was filed Jan. 11, 1996, the contents of which are incorporated herein in their entirety by reference (which corresponds to U.S. Pat. No. 5,932,462, which is also incorporated by reference). These branched PEGs can then be modified in accordance with the teachings herein.

Many water soluble substantially non-immunogenic polymers other than PEG are also suitable for the present invention. These other polymers can be either in linear form or branched form, and include, but are not limited to, other poly(alkylene oxides) such as poly(propylene glycol) ("PPG"), copolymers of ethylene glycol and propylene glycol and the like; poly(vinyl alcohol) ("PVA") and the like. The polymers can be homopolymers or random or block copolymers and texpolymers based on the monomers of the above polymers, straight chain or branched.

Specific examples of suitable additional polymers include, but are not limited to, difunctional poly (acryloylmorpholine) ("PAcM"), and poly (vinylpyrrolidone)("PVP"). PVP and poly(oxazoline) are well known polymers in the art and their preparation should be readily apparent to the skilled artisan. PAcM and its synthesis and use are described in U.S. Pat. Nos. 5,629,384 and 5,631,322, the contents of which are incorporated herein by reference in their entirety.

Although the molecular weight of each chain of the polymer backbone can vary, it is typically in the range of from about 100 to about 100,000, preferably from about 6,000 to about 80,000.

Those of ordinary skill in the art will recognize that the foregoing list for substantially water soluble non-immunogenic polymer backbones is by no means exhaustive and is merely illustrative, and that all polymeric materials having the qualities described above are contemplated.

The activated polymer of this invention also has proximal reactive groups linked to at least one arm of the polymer backbone. As will be apparent, the term "proximal" is used herein to mean that the terminus has two free reactive moieties capable of reacting with two other moieties in another molecule or two other molecules, which can be the same or different.

The terminus typically has a branching moiety covalently linked to a polymer chain of the polymer backbone through a hydrolytically stable linkage. Typically, there are two free reactive groups branching out from the branching moiety. The term "free" as used herein means that each of the two free reactive groups has two ends, one of which is covalently linked to the branching moiety and the other end is not linked to any other moiety or group through covalent linkage, and (available for reaction with another moiety or group, e.g., of another molecule).

Typically the branching moiety is a stable, non-reactive, and inert moiety that is covalently linked to a polymer chain and to the two reactive groups. The branching moiety should not form a hydrogen bond or ionic bond with metal ions or moieties or molecules. It is believed that the ability to form strong hydrogen bonds or ionic bonds would interfere with the branching moiety's function. The branching atom, i.e., the atom the two free reactive groups are linked to is not a nitrogen atom (N), but is typically a carbon atom (C).

At least one of the two free reactive groups may comprise two portions: a reactive moiety at the free end and a tethering group linking the reactive moiety to the branching moiety. The reactive moiety is a moiety capable of reacting with a moiety in another molecule, e.g., a biologically active agent such as a protein, a peptide, etc. Examples of suitable reactive moieties include, but are not limited to, active esters, active carbonates, aldehydes, isocyanates, isothiocyanates, epoxides, alcohols, maleimides, vinylsulfones, hydrazides, dithiopyridines, N-succinimidyl, and iodoacetamides. The selection of a free reactive moiety is determined by the moiety in another molecule to which the free reactive moiety is to react. For example, when the moiety in another molecule is a thiol moiety, then a vinyl sulfone moiety is preferred for the free reactive moiety of the activated polymer. On the other hand, an N-succinimidyl moiety is preferred to react to an amino moiety in a biologically active agent.

The tethering group can have a predetermined length such that the reactive moiety linked to it is at a predetermined distance away from the branching moiety, and consequently, a predetermined distance from the other reactive moiety of the terminus. Typically, the tethering group is non-reactive and is a substantially linear chain of atoms, e.g., alkyl chains, ether chains, ester chains, amide chains, and combinations thereof.

Thus, in a preferred embodiment, the activated polymer of this invention can be represented by formula I:

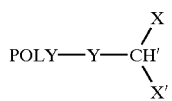

or formula II:

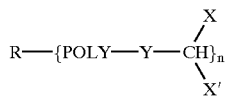

In the above formula, POLY is a linear polymer chain of a water soluble substantially non-immunogenic polymer backbone, preferably is poly(ethylene glycol) or a derivative thereof. In the activated polymer represented by formula I, the polymer backbone has only one polymer chain. Y is a hydrolytically stable linkage, which can comprise an atom or a group such as —O—, —S—and —CO—NH—. It will be apparent to skilled artisan that many other hydrolytically stable linkages can also be employed in this embodiment.

X and X' are free reactive groups, which can be same or different, each having a reactive moiety capable of reacting with a moiety in another molecule such as a protein. In the activated polymer as represented by formula I, the polymer backbone POLY can have a capping group at the end opposite to the terminus having proximal reactive groups. The capping group can be, for example, —OH, various alkyl, and can also contain proximal reactive groups —Y—CHXX' wherein Y, X and X' are as described above. Accordingly, the activated polymer can have two terminals with proximal reactive groups, one on each end of the polymer backbone.

In formula II, R is the central core as described above. POLY is a polymer chain of the water soluble substantially non-immunogenic polymer backbone. Y is a hydrolytically stable linkage. n is from 2 to 200 representing the number of polymer chains or arms in the polymer backbone, as described above.

As will be apparent, the branching moiety as described above is CH in this embodiment of the activated polymer. Typically it does not become charged in normal conditions, and does not form an ionic bond with a metal ion.

In a preferred embodiment, X and X' can have a tethering group in addition to a reactive moiety and can be represented by —W—Z and —W'—Z' respectively, in which Z and Z' represent free reactive moieties for conjugating the polymer to another molecule. W and W' represent tethering groups. Z and Z' can be different or same reactive moieties.

Some examples of preferred embodiments of the activated polymers of this invention are provided as follows:

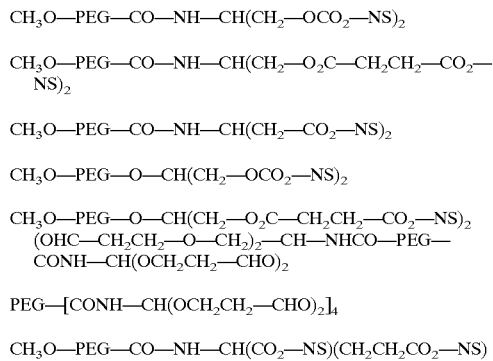

In these examples, —NS represents the N-succinimidyl moiety.

In accordance with another aspect of this invention, a method for preparing the activated water soluble polymer of this invention is also provided.

Typically, in the first step, there is a first intermediate polymer provided having a polymer backbone and a reactive end group covalently linked to the polymer backbone.

In addition, a compound having three reactive groups linked to a branching moiety is provided. This compound typically has a branching moiety forming a central core and three free groups branching out from the central core. When the three free groups are linked to the same atom in the branching moiety, the atom is not a nitrogen atom. One of the three free groups can react with the reactive end group of the first intermediate polymer to form a hydrolytically stable linkage. The other two free groups can be ultimately converted into the two free reactive groups on the terminus of the activated polymer of this invention. Examples of these compounds include, $H_2NCH(CH_2-OH)_2$, NaO—CH $(CH_2-O-Bz)_2$, $H_2N-CH(CH_2CO_2H)_2$, and the like. As will be apparent, in these examples, the branching moiety is CH. The $H_2N-$ and NaO— moieties can be used to link the compound to the first intermediate polymer to form a hydrolytically stable linkage, while the hydroxyl groups, carboxylic acid groups, and $-CH_2-O-Bz$ groups can be ultimately converted into free reactive moieties of the activated polymer of this invention.

Thus, in the second step of the method, the compound having three reactive groups is reacted with the first intermediate polymer to form a second intermediate polymer which includes a hydrolytically stable linkage linking the first intermediate polymer and the compound having three reactive groups, thus leaving only two free groups at the terminus of the polymer chain.

In the third step, the two free groups of the compound are converted into two free reactive moieties linked to the branching moiety. A number of methods known in the art can be employed in the conversion. For example, the free groups can be reacted to a compound which can impart a free reactive moiety. Alternatively, the two free groups in the second intermediate polymer can be oxidized or reduced or substituted to form two new free reactive moieties. Such methods will be apparent to skilled artisan in view of the Examples given below.

In accordance with yet another aspect of this invention, a conjugate is provided formed by covalently linking the activated water soluble polymer of this invention to another molecule, e.g., a biologically active agent. Typically, a suitable biologically active agent can be any biologically active agent having a moiety capable of reacting with at least one of the two proximal reactive groups in the terminus of the activated polymer.

The biologically active agent can have two such moieties and each of them can be linked to one of the two reactive groups. Alternatively, the conjugate can have two biologically active agents each being linked to one of the two reactive moieties of the activated polymer. For example, the reactive moieties in the activated polymer can be vinyl sulfone moieties, which can react with a thiol moiety. If a protein has only one thiol moiety, then two of such protein molecules can be linked to the activated polymer through the two vinyl sulfone moieties. When a protein has two thiol moieties, the reaction between the protein and the activated polymer can be controlled such that each activated polymer molecule is conjugated to two protein molecules. Alternatively, the reaction can also be controlled such that the two vinyl sulfone moieties of an activated polymer are reacted with two thiol moieties on the same protein molecule.

Other moieties in biologically active agents useful for reacting with the free reactive moieties of the bivalent terminus of an activated polymer of this invention include, e.g., amino groups, carboxylic acid groups, etc. It will be apparent to the skilled artisan once apprised of the present invention to select appropriate free reactive moieties in an activated polymer for reaction with a given moiety in a biologically active agent. For example, if conjugation is through reaction with an amino group in a biologically active agent, moieties such as $-CO_2-NS$ or aldehyde are preferably used as a free reactive moiety in the activated polymer for conjugation.

Because activated polymers having different tethering groups can be prepared in accordance with this invention, an activated polymer can be provided in which the two reactive groups in a bivalent terminus of the activated polymer are in a desirable distance from each other. When such an activated polymer is conjugated to two biologically active agent molecules, the two molecules can be held at a desired distance apart.

The following examples are given to illustrate the invention, but should not be considered in limitation of the invention:

Example 1. Synthesis of $mPEG_{20K}-OCH_2CH_2CONHCH(CH_2O_2CCH_2\ CH_2CO_2NS)_2$
(NS=N-succinimidyl)

Example 2. Synthesis of $mPEG_{20K}-OCH(CH_2-SO_2CH=CH_2)_2$

Example 3. Synthesis of $mPEG_{5K}-O_2CNH-CH(CH_2CO_2NS)_2$

Example 4. Synthesis of $mPEG_{5K}-O-CH_2CH_2CH(CO_1H)_2$

EXAMPLE 1

Reactions:
1. $mPEG_{20K}-OCH_2CH_2CO_2NS+H_2NCH(CH_2-OH)_2 \rightarrow mPEG_{20K}-OCH_2CH_2CONHCH(CH_2OH)_2+NHS$
   NS=N-succinimidyl;
   NHS=N-hydroxysuccinimide
2. $mPEG_{20K}-OCH_2CH_2CONHCH(CH_2-OH)_{2+2}SA \rightarrow mPEG_{20K}-OCH_2CH_2CONHCH(CH_2-O_2CCH_2CH_2CO_2H)_2$
   SA=succinic anhydride
3. $mPEG_{20K}-OCH_2CH_2CONHCH(CH_2-O_2CCH_2CH_2CO_2H)_2+NHS+DCC \rightarrow mPEG_{20K}-OCH_2CH_2CONHCH(CH_2-O_2CCH_2CH_2CONS)_2$
   DCC=dicyclohexylcarbodiimide Preparations:
1. $mPEG_{20K}-OCH_2CH_2CONHCH(CH_2OH)_2$ A solution of $mPEG_{20K}-OCH_2CH_2CO_2NS$ (mSPA 20K, 20 g, 0.001 moles), $H_2NCH(CH_2-OH)_2$ (serinol, 0.14 g, 0.00154 moles), and triethylamine (0.3 ml) in acetonitrile (100 ml) was stirred under nitrogen overnight and the solvent removed by distillation. The product was chromatographed on DEAE sepharose eluted with water and the eluate was saturated with NaCl and extracted with chloroform. The resulting chloroform phase was dried over magnesium sulfate, filtered, and the filtrate evaporated to dryness under vacuum to yield 20 g of product as a white solid showing a single peak with gel permeation chromatography (Ultrahydrogel 250, pH 7.2 buffer).

2. $mPEG_{20K}-OCH_2CH_2CONHCH(CH_2-O_2CCH_2CH_2CO_2H)_2$

A solution of the product from (1) (20 g, 0.002 moles) and butylated hydroxytoluene (BHT) (0.02 g) in 220 ml of chloroform was subjected to distillation until about 150 ml of solvent had distilled. Succinic anhydride (2.0 g, 0.02 moles), pyridine (1.62 ml, 0.02 moles), and 40 ml of toluene were added and the resulting mixture heated at 84° C. for 20 h under nitrogen. The product was precipitated with 850 ml of ether and collected by filtration. After drying, the product was dissolved in 200 ml of water, 20 g of NaCl added, and the pH adjusted to 3 with aqueous phosphoric acid. The product was extracted with chloroform (200+150+100 ml) and the combined extracts dried over magnesium sulfate. Evaporation of the dried solution yielded the product as a white solid (16 g). The molecular weight was determined to be 20,940 Da by potentiometric titration.

3. $mPEG_{20K}-OCH_2CH_2CONHCH(CH_2-O_2CCH_2CH_2CONS)_2$

A solution of the product from (2) (15 g, 0.0015 moles), N-hydroxysuccinimide (0.21 g, 0.00179 moles), dicyclohexylcarbodiimide, 0.37 g, 0.00177 moles) in methylene chloride (100 ml) was stirred at room temperature under nitrogen overnight. The suspension was filtered, product precipitated twice from methylene chloride by addition of ether (850 ml) and collected by filtration to obtain a white solid (13.0 g) which had 97.7% substitution by proton nmr. The proton nmr displayed a broad multiplet at 3.50 ppm (PEG backbone methylene groups), a singlet at 3.23 ppm PEG methyl), a singlet at 2.80 ppm (NS methylenes), and multiplets at 2.68 and 2.95 ppm (succinate methylenes).

EXAMPLE 2

Reactions:
1. $HO-CH(CH_2-O-Bz)_2+NaH$ (toluene)$\rightarrow NaO-CH(CH_2 OBz)_2$
   Bz=Benzyl
2. $NaO-CH(CH_2-O-Bz)_2+mPEG_{20K}-O-Ms \rightarrow mPEG_{20K}O-CH(CH_2OBZ)_2$
   Ms=mesylate
3. $mPEG_{20K}O-CH(CH_2OBZ)_2+HCO_2H/MeOH/H_2O/Pd/C \rightarrow mPEG_{20K}O-CH(CH_2OH)_2$
4. $mPEG_{20K}O-CH(CH_2OH)_2+MsCl/Et_3N \rightarrow mPEG_{20K}O-CH(CH_2OMs)_2$
5. $mPEG_{20K}O-CH(CH_2OMs)_2+HSCH_2CH_2OH \rightarrow mPEG_{20K}O-CH(CH_2SCH_2CH_2OH)_2$
6. $mPEG_{20K}O-CH(CH_2SCH_2CH_2OH)_2+H_2WO_4 \rightarrow mPEG_{20K}O-CH(CH_2SO_2CH_2CH_2OH)_2$
7. $mPEG_{20K}O-CH(CH_2SO_2CH_2CH_2OH)_2+MsCl/Et_3N \rightarrow mPEG_{20K}O-CH(CH_2SO_2CH=CH_2)_2$ Preparations:
1. $mPEG_{20K}O-CH(CH_2OBZ)_2$ A solution of 18 g (0,0641 moles) of 1,3-dibenzyloxy-2-propanol in 80 ml of toluene was distilled until 15 ml of toluene was removed. The azeotropically dried solution was then added to a suspension of 2.56 g (0.064 moles) of NaH in 80 ml of toluene and the resulting mixture stirred while heating to 37–40° C. before filtering. The filtrate was then added to a solution of azeotropically-dried mPEG$_{20K}$ mesylate in about 350 ml of toluene and the resulting mixture was heated for 20 h at 125° C. under N$_2$. The product was precipitated with cold ether, wash on the filter with hexane, and dried under vacuum to yield 70.4 g of white solid shown to be pure by proton nmr.

2. $mPEG_{20K}O-CH(CH_2OH)_2$

To a solution of 15 g (0.00075 moles) of the product from (1) in 9.2 ml of formic acid and 0.8 ml of water was added 2.0 g of Pd/C (10%) and the mixture was stirred for 2 h under nitrogen. The mixture was then filtered and the pH of the filtrate adjusted to 7.2. The resulting solution was extracted with CH$_2$Cl$_2$ and the extract dried over MgSO$_4$. Evaporation of the solution yielded 12.9 g of product which displayed no benzyl groups in the proton nmr.

3. $mPEG_{20K}O-CH(CH_2OMs)_2$

To an azeotropically-dried solution of the product from (2) (8.0 g, 0.000889 moles) in toluene (100 ml) containing 0.008 g of BHT was added a solution of mesyl chloride (0.090 ml, 0.00116 moles) and triethylamine (0.210 ml, 0.0011 moles) in 10 ml of ET$_3$N and the resulting solution was stirred overnight at room temperature under nitrogen. Ethanol (1 ml) was added and 50 ml of the solvent was removed by distillation before adding 500 ml of ether to precipitate the product. The product was collected by filtration and dried under vacuum to yield 7.6 g of the mesylate derivative shown by nmr to be 100% substituted.

4. $mPEG_{20K}O-CH(CH_2SCH_2CH_2OH)_2$

A solution of the product of (3), (7.0 g, 0.00035 moles), mercaptoethanol (0.56, 0.0080 moles), NaOH (0.22 g), in toluene (30 ml) and ethanol (60 ml) was heated at 60° C. for 2 h under N$_2$. The pH was adjusted to 7 and the product extracted with methylene chloride (3×100 ml). After drying the extract over MgSO$_4$, the solvent was removed and the product precipitated with 250 ml of ethyl ether. The product was collected by filtration and dried under vacuum to get 6.6 g of white solid which was shown by nmr to be 97.3% substituted.

5. $mPEG_{20K}O-CH(CH_2SO_2CH_2CH_2OH)_2$

A solution containing the product from (4), 6.5 g (0.00065 moles), and tungstic acid (0.16 g) in water (14 ml) was prepared and the pH adjusted to 6.6. Hydrogen peroxide (30%, 0.65 ml) was added and the mixture stirred at room temperature overnight. The pH was adjusted to 7.5 and the mixture stirred 1 h before extracting with CH$_2$Cl$_2$ (3×30 ml). The mixture was dried over MgSO$_4$, filtered, and the filtrate concentrated to 25 ml. The product was precipitated with 200 ml of ether and collected by filtration to obtain 5.3 g of product after vacuum drying. The product was shown by nmr to have 86% substitution.

6. $mPEG_{20K}O-CH(CH_2SO_2CH=CH_2)_2$

A solution of the product from (5), (5.2 g, 0.00052 moles), Et$_3$N (0.63 ml, 0.00452 moles), BHT (0.005 g), and MsCl (0.15 ml, 0.001938 moles) in CH$_2$Cl$_2$ (25 ml) was stirred at room temperature for 42 h at room temperature. Ethanol (1 ml) was added and the mixture was stirred 15 minutes. Methylene chloride (50 ml) was added and the resulting solution was washed with aqueous 1M HCl followed by 5% aqueous Na$_2$HPO$_4$. After drying over MgSO$_4$, the solution was concentrated to 30 ml and the product precipitated with 300 ml of ether. The product was collected by filtration and dried under vacuum to yield the product (4.6 g) as a white solid. The degree of substitution was 92.5% by nmr. The $^1$H nmr spectrum (dmso-d6) displayed absorptions at 3.51 ppm (PEG backbone CH$_2$), 3.23 ppm (CH$_3$O), 6.2 and 7.0 ppm (m, vinyl H). Note in this example that Y=O, W=CH$_2$, and Z=SO$_2$CH=CH$_2$.

EXAMPLE 3

Reactions:
1. $mPEG_{5K}BTC+H_2N-CH(CH_2CO_2H)_2 \rightarrow mPEG_{5K}O_2CNHCH(CH_2CO_2H)_2$
   BTC=1-benzotriazolyl carbonate
2. $mPEG_{5K}O_2CNHCH(CH_2CO_2H)_2+NHS/DCC \rightarrow mPEG_{5K}O_2CNHCH(CH_2CO_2NS)_2$ Preparations:
1. $mPEG_{5K}O_2CNHCH(CH_2CO_2H)_2$ To a solution of β-glutamic acid (0.10 g, 0.00068 moles), boric acid (0.1 g) in 10 ml of water at pH 8 was added mPEG$_5$KBTC over 15 m while maintaining the pH at 8.15–8.25 by addition of NaOH solution. NaCl (6 g) was added and the pH of the solution was adjusted to 2 with 10% H$_3$PO$_4$. The product was extracted into CH$_2$Cl$_2$ (100+80+50 ml) and the combined extracts were dried over MgSO$_4$. The mixture was filtered and the filtrate evaporated under vacuum to yield 7.8 g of product. The mixture was determined to be 75.5% of the MPEG glutamic acid derivative and 24.5% MPEG. This mixture was purified by chromatography on DEAE sepharose by first eluting with water and then eluting the desired product with 0.5 M NaCl. Extraction of the product from the NaCl solution (pH 2) with methylene chloride followed by drying the extract over MgSO$_4$ and evaporation of the solvent yielded 6.1 g of material shown to be 100% pure by GPC.

2. $mPEG_{5K}O_2CNHCH(CH_2CO_2NS)_2$

A solution of mPEG$_{5K}$O$_2$CNHCH(CH$_2$CO$_2$H)$_2$ (6.0 g, 0.00116 moles), NHS (0.385 g, 0.001627 moles), DCC (0.676 g, 0.00162 moles) in methylene chloride (50 ml) was stirred overnight at room temperature under nitrogen. The resulting suspension was filtered and the filtrate was added to 500 ml of cold ethyl ether. The precipitate was collected by filtration and dried under vacuum to obtain 5.5 g of product which was shown by nmr to have 100% substitution. The $^1$H nmr spectrum (dmso-d6) displayed absorptions at 3.51 ppm (PEG backbone CH$_2$), 3.23 ppm (CH$_3$O), 4.29 ppm (—NHCH—), 4.05 ppm (—CH$_2$—O—CONH—), 3.24 ppm (CH$_2$CO$_2$NS), 2.81 (NS CH$_2$).

EXAMPLE 4

Reactions:

1.

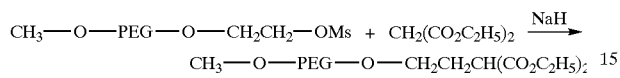

2.

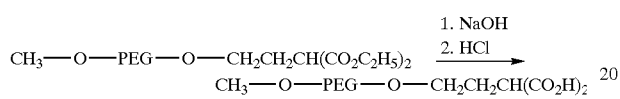

3.

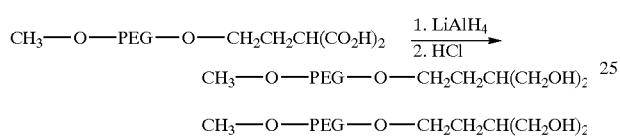

Preparations:

1. Preparation of CH$_3$—O—PEG—O—CH$_2$CH$_2$CH(CO$_2$H)$_2$ (Steps 1 and 2 above)

Diethyl malonate (8.8 ml) in 150 ml of dry dioxane was added dropwise to NaH (2.4 g) in 60 ml of toluene under argon. MPEG$_{5000}$ mesylate (30 g) in 250 ml of toluene was azeotropically distilled to remove 150 ml of toluene and the residue was added to the above diethyl malonate solution. After refluxing the mixture for 3–4 hours, it was evaporated under vacuum to dryness and dried in vacuo overnight. The dried material was then dissolved in 200 ml of 1N NaOH, the solution was stirred for 2 days at room temperature, and the pH adjusted to 3 with 1N HCl. NaCl was added to the solution to a concentration of about 15% and the mixture was then extracted with 350 ml of CH$_2$Cl$_2$ in several portions. The combined extracts were dried over Na$_2$SO$_4$, concentrated under vacuum and the product precipitated by addition of isopropanol/ether (1:1). The product was collected by filtration and dried under vacuum overnight to obtain 24.7 g of product as a white powder. GPC (Ultrahydrogel 250) showed the product to be 98% pure.

$^1$H NMR (dmso-d6, ppm): 1.96 (t, CH$_2$CH$_2$—C); 3.51 (br m, PEG —CH$_2$CH$_2$—O—).

2. Preparation of CH$_3$—O—PEG$_{5000}$—O—CH$_2$CH$_2$CH(CH$_2$OH)$_2$

CH$_3$—O—PEG$_{5000}$—O—CH$_2$CH$_2$CH(CO$_2$H)$_2$ (5 g) was dissolved in 50 ml of toluene and 9.8 ml of LiAlH$_4$ (1 M in THF) was added. After stirring overnight at room temperature, the mixture was evaporated to dryness under vacuum and 150 ml of water and 22.5 g of NaCl were added. The pH was adjusted to 6.5 with aqueous HCl and the resulting solution was extracted with 3×50 ml of methylene chloride. The combined extracts were dried over Na$_2$SO$_4$ and the solution was evaporated to dryness. The product was precipitated with ethyl ether and collected by filtration. After chromatography on DEAE sepharose, the product was 90% pure by GPC (Ultrahydrogel 250).

$^1$H NMR (dmso-d6, ppm): 3.51 (br m, PEG —CH$_2$CH$_2$—O—); 1.5 (br mult, CH; 4.32 (t, OH).

What is claimed is:

1. A conjugate comprising:
   a biologically active agent; and
   an activated, water soluble polymer comprising a polymer backbone having at least one terminus bonded to a branching atom through a hydrolytically stable linkage, the branching atom being covalently bonded to at least two reactive groups, each reactive group comprising a reactive moiety,
   said biologically active agent being covalently linked to at least one of said reactive groups, wherein the water soluble polymer does not hydrolyze.

2. The conjugate of claim 1, wherein said biologically active agent is selected from the group consisting of proteins, peptides, lipids, polysaccharides, nucleotides, and derivatives thereof.

3. The conjugate of claim 1, wherein said biologically active agent has a free amine or thiol group and at least one of said reactive groups comprises an amine-reactive or thiol-reactive moiety.

4. The conjugate of claim 1, wherein the branching atom is a carbon atom.

5. The conjugate of claim 1, wherein said terminus of the backbone is bonded to the structure:

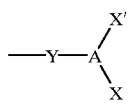

wherein Y is a hydrolytically stable linkage, A is a branching atom, and X and X', which may be the same or different, are reactive groups comprising a reactive moiety.

6. The conjugate of claim 5, wherein A is CH.

7. The conjugate of claim 5, wherein at least one of said X and X' has the structure —W—Z, wherein W is a tethering group and Z is said reactive moiety.

8. The conjugate of claim 7, wherein W is selected from the group consisting of alkyl chains, ether chains, ester chains, amide chains, and combinations thereof.

9. The conjugate of claim 7, wherein W is selected from the group consisting of —(CH$_2$)$_m$—, —(CH$_2$)$_m$—O—, —O—(CH$_2$)$_m$—, —(CH$_2$)$_m$—O$_2$C—CH$_2$CH$_2$—, and —(CH$_2$)$_m$—O—(CH$_2$)$_r$—, wherein m and r are independently 1–10.

10. The conjugate of claim 7, wherein Z is selected from the group consisting of active esters, active carbonates, aldehydes, isocyanates, isothiocyanates, epoxides, alcohols, maleimides, vinylsulfones, hydrazides, dithiopyridines, and iodoacetamides.

11. The conjugate of claim 7, wherein Z is selected from the group consisting of—OH, —CO$_2$H, —CHO, —SO$_2$—CH═CH$_2$, and —CO$_2$—Q, wherein Q is N-succinimidyl, sulfo-N-succinimidyl, or 1-benzotriazolyl.

12. The conjugate of claim 1, wherein said reactive moiety is selected from the group consisting of active esters, active carbonates, aldehydes, isocyanates, isothiocyanates, epoxides, alcohols, maleimides, vinylsulfones, hydrazides, dithiopyridines, and iodoacetamides.

13. The conjugate of claim 1, wherein said reactive moiety is selected from the group consisting of—OH, —CO$_2$H, —CHO, —SO$_2$—CH═CH$_2$, and —CO$_2$—Q, wherein Q is N-succinimidyl, sulfo-N-succinimidyl, or 1-benzotriazolyl.

14. The conjugate of claim 1, wherein said polymer backbone is selected from the group consisting of linear or branched poly(alkylene oxide), linear or branched poly (vinyl pyrrolidone), linear or branched poly(vinyl alcohol), linear or branched polyoxazoline, and linear or branched poly(acryloylmorpholine).

15. The conjugate of claim 1, wherein said polymer backbone has a molecular weight of about 100 to about 100,000 Da.

16. The conjugate of claim 15, wherein said polymer backbone has a molecular weight of about 6,000 to about 80,000 Da.

17. The conjugate of claim 1, wherein said polymer backbone is a poly(alkylene oxide) selected from the group consisting of poly(ethylene glycol), poly(propylene glycol), and copolymers of ethylene glycol and propylene glycol.

18. The conjugate of claim 1, wherein said polymer backbone is poly(ethylene glycol) having a molecular weight of about 200 to about 100,000 Da.

19. The conjugate of claim 1, wherein the hydrolytically stable linkage is selected from the group consisting of —O—, —S— and —CO—NH—.

20. The conjugate of claim 1, wherein the at least two reactive groups have the structure —W—Z and —W'—Z', respectively, wherein Z and Z' are said reactive moieties, and W and W' are tethering groups.

21. The conjugate of claim 20, wherein W and W' are selected from the group consisting of alkyl chains, ether chains, ester chains, amide chains, and combinations thereof.

22. The conjugate of claim 20, wherein W and W' are independently selected from the group consisting of —$(CH_2)_m$—, —$(CH_2)_m$—O—, O—$(CH_2)_m$—, —$(CH_2)_m$—$O_2C$—$CH_2CH_2$—, and —$(CH_2)_m$—O—$(CH_2)_r$—, wherein m and r are independently 1–10.

23. The conjugate of claim 20, wherein Z and Z' are each independently selected from the group consisting of active esters, active carbonates, aldehydes, isocyanates, isothiocyanates, epoxides, alcohols, maleimides, vinylsulfones, hydrazides, dithiopyridines, and iodoacetamides.

24. The conjugate of claim 20, wherein Z and Z' are each independently selected from the group consisting of —OH, —$CO_2H$, —CHO, —$SO_2$—CH=$CH_2$, and —$CO_2$—Q, wherein Q is N-succinimidyl, sulfo-N-succinimidyl, or 1-benzotriazolyl.

25. The conjugate of claim 1, wherein said polymer has the structure:

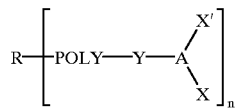

wherein
R is a central core;
POLY is a polymer backbone;
A is a branching atom;
Y is a hydrolytically stable linkage;
n is from 2 to 200; and
X and X' are reactive groups comprising a reactive moiety.

26. The conjugate of claim 25, wherein at least one of said X and X' has the structure —W—Z, wherein W is a tethering group and Z is said reactive moiety.

27. The conjugate of claim 26, wherein W is selected from the group consisting of alkyl chains, ether chains, ester chains, amide chains, and combinations thereof.

28. The conjugate of claim 26, wherein W is selected from the group consisting of —$(CH_2)_m$—, —$(CH_2)_m$—O—, —O—$(CH_2)_m$—, —$(CH_2)_m$—$O_2C$—$CH_2CH_2$—, and —$(CH_2)_m$—O—$(CH_2)_r$—, wherein m and r are independently 1–10.

29. The conjugate of claim 26, wherein Z is selected from the group consisting of active esters, active carbonates, aldehydes, isocyanates, isothiocyanates, epoxides, alcohols, maleimides, vinylsulfones, hydrazides, dithiopyridines, and iodoacetamides.

30. The conjugate of claim 26, wherein Z is selected from the group consisting of —OH, —$CO_2H$, —CHO, —$SO_2$—CH=$CH_2$, and —$CO_2$—Q, wherein Q is N-succinimidyl, sulfo-N-succinimidyl, or 1-benzotriazolyl.

31. The conjugate of claim 25, wherein each POLY is selected from the group consisting of linear or branched poly(alkylene oxide), linear or branched poly(vinyl pyrrolidone), linear or branched poly(vinyl alcohol), linear or branched polyoxazoline, and linear or branched poly(acryloylmorpholine).

32. The conjugate of claim 25, wherein each POLY has a molecular weight of about 100 to about 100,000 Da.

33. The conjugate of claim 32, wherein each POLY has a molecular weight of about 6,000 to about 80,000 Da.

34. The conjugate of claim 25, wherein each POLY is a poly(alkylene oxide) selected from the group consisting of poly(ethylene glycol), poly(propylene glycol), and copolymers of ethylene glycol and propylene glycol.

35. The conjugate of claim 34, wherein each POLY is poly(ethylene glycol) having a molecular weight of about 200 to about 100,000 Da.

36. The conjugate of claim 25, wherein R is a moiety selected from the group consisting of lysine, glycerol, pentaerythritol, and sorbitol.

37. The conjugate of claim 25, wherein each Y is selected from the group consisting of —O—, —S— and —CO—NH—.

38. The conjugate of claim 25, wherein X and X' are —W—Z and —W'—Z', respectively, wherein Z and Z' are said reactive moieties, and W and W' are tethering groups.

39. The conjugate of claim 38, wherein W and W' are selected from the group consisting of alkyl chains, ether chains, ester chains, amide chains, and combinations thereof.

40. The conjugate of claim 38, wherein W and W' are independently selected from the group consisting of —$(CH_2)_m$—, $(CH_2)_m$—O—, —O—$(CH_2)_m$—, —$(CH_2)_m$—$O_2C$—$CH_2CH_2$—, and —$(CH_2)_m$—O—$(CH_2)_r$—, wherein m and r are independently 1–10.

41. The conjugate of claim 38, wherein Z and Z' are each independently selected from the group consisting of active esters, active carbonates, aldehydes, isocyanates, isothiocyanates, epoxides, alcohols, maleimides, vinylsulfones, hydrazides, dithiopyridines, and iodoacetamides.

42. The conjugate of claim 38, wherein Z and Z' are each independently selected from the group consisting of —OH, —$CO_2H$, —CHO, —$SO_2$—CH=$CH_2$, and —$CO_2$—Q, wherein Q is N-succinimidyl, sulfo-N-succinimidyl, or 1-benzotriazolyl.

43. The conjugate of claim 1, wherein the polymer has a formula selected from the group consisting of:

$CH_3O$—PEG—CO—NH—$CH(CH_2$—$OCO_2$—$NS)_2$, $CH_3O$—PEG—CO—NH—$CH(CH_2$—$O_2C$—$CH_2CH_2$—$CO_2$—$NS)_2$, $CH_3O$—PEG—CO—NH—$CH(CH_2$—$CO_2$—$NS)_2$,

CH₃O—PEG—O—CH(CH₂—OCO₂—NS)₂,

CH₃O—PEG—O—CH(CH₂—O₂C—CH₂CH₂—CO₂—NS)₂, (OHC—CH₂CH₂—O—CH₂)₂—CH—NHCO—PEG—CONH—CH(OCH₂CH₂—CHO)₂,

PEG—[CONH—CH(OCH₂CH₂—CHO)₂]₄,

CH₃O—PEG—CO—NH—CH(CO₂—NS)[CH₂CH₂CO₂—NS],

CH₃O—PEG—O—CH₂CH₂CH(CO₂H)₂,

CH₃O—PEG—O—CH₂CH₂CH(CH₂OH)₂, and

CH₃O—PEG—O₂CNHCH(CH₂CO₂H)₂, wherein NS is N-succinimidyl.

44. The conjugate of claim 1, wherein the polymer backbone is branched poly(ethylene glycol) and the reactive groups are selected from the group consisting of active esters, active carbonates, aldehydes, isocyanates, isothiocyanates, epoxides, alcohols, maleimides, vinylsulfones, hydrazides, dithiopyridines, and iodoacetamides.

45. The conjugate of claim 1, wherein the polymer backbone comprises methoxy poly(ethylene glycol) disubstituted lysine.

46. The conjugate of claim 1, wherein the polymer backbone has the structure:

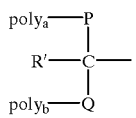

wherein $poly_a$ and $poly_b$ are water-soluble and non-peptidic polymer backbones;

R' is a nonreactive moiety; and

P and Q are nonreactive linkages.

47. The conjugate of claim 46, wherein $poly_a$ and $poly_b$ are both methoxy poly(ethylene glycol).

48. The conjugate of claim 46, wherein R' is H, methyl or a water-soluble and non-peptidic polymer backbone.

49. The conjugate of claim 46, wherein the polymer backbone is bonded to the structure:

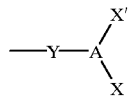

wherein Y is a hydrolytically stable linkage, A is a branching atom, and X and X', which may be the same or different, are reactive groups comprising a reactive moiety.

50. The conjugate of claim 49, wherein A is CH.

51. The conjugate of claim 49, wherein at least one of said X and X' has the structure —W—Z, wherein W is a tethering group and Z is said reactive moiety.

52. The conjugate of claim 51, wherein X and X' have the structure —W—Z and —W'—Z', respectively, wherein Z and Z' are said reactive moieties, and W and W' are tethering groups.

53. The conjugate of claim 52, wherein Z and Z' are each independently selected from the group consisting of active esters, active carbonates, aldehydes, isocyanates, isothiocyanates, epoxides, alcohols, maleimides, vinylsulfones, hydrazides, dithiopyridines, and iodoacetamides.

* * * * *